United States Patent
Halfmann et al.

(10) Patent No.: US 8,796,640 B2
(45) Date of Patent: Aug. 5, 2014

(54) RADIATING ELEMENT FOR IRRADIATING SURFACES, HAVING A SOCKET

(75) Inventors: Helmut Halfmann, Rheinberg (DE); Axel Hombach, Kuerten (DE); Markus Roth, Bonn (DE)

(73) Assignee: Osram AG, Munich (DE)

( * ) Notice: Subject to any disclaimer, the term of this patent is extended or adjusted under 35 U.S.C. 154(b) by 0 days.

(21) Appl. No.: 13/812,522

(22) PCT Filed: Oct. 26, 2011

(86) PCT No.: PCT/EP2011/068766
§ 371 (c)(1),
(2), (4) Date: Jan. 28, 2013

(87) PCT Pub. No.: WO2012/059382
PCT Pub. Date: May 10, 2012

(65) Prior Publication Data
US 2013/0119279 A1 May 16, 2013

(30) Foreign Application Priority Data
Nov. 2, 2010 (DE) .......... 10 2010 043 215

(51) Int. Cl.
*A61L 2/10* (2006.01)
(52) U.S. Cl.
USPC .... 250/432 R; 250/428; 250/435; 250/492.1; 250/493.1; 250/504 R
(58) Field of Classification Search
USPC ............ 250/428, 432 R, 435, 492.1, 493.1, 250/504 R; 315/607, 567
See application file for complete search history.

(56) References Cited

U.S. PATENT DOCUMENTS

| | | | | |
|---|---|---|---|---|
| 4,948,980 A * | 8/1990 | Wedekamp | | 250/504 R |
| 5,013,959 A * | 5/1991 | Kogelschatz | | 313/36 |
| 5,198,717 A | 3/1993 | Kogelschatz et al. | | |
| 5,200,156 A * | 4/1993 | Wedekamp | | 422/186.3 |
| 5,214,344 A | 5/1993 | Kogelschatz | | |
| 5,604,410 A | 2/1997 | Vollkommer et al. | | |
| 5,757,132 A * | 5/1998 | Matsuno et al. | | 313/607 |
| 6,373,192 B1 | 4/2002 | Morimoto et al. | | |
| 6,379,024 B1 * | 4/2002 | Kogure et al. | | 362/263 |
| 6,624,428 B2 | 9/2003 | Hishinuma | | |
| 6,628,078 B2 * | 9/2003 | Inayoshi | | 313/607 |
| 6,657,392 B2 | 12/2003 | Hitzschke et al. | | |
| 6,734,444 B2 | 5/2004 | Fujitugu | | |
| 7,008,970 B2 * | 3/2006 | Kong et al. | | 518/728 |
| 7,224,111 B2 | 5/2007 | Kling et al. | | |
| 8,404,183 B2 * | 3/2013 | Sahle-Demessie et al. | | 422/22 |

(Continued)

FOREIGN PATENT DOCUMENTS

| | | | |
|---|---|---|---|
| DE | 3232537 A1 | 3/1984 | |
| EP | 0489184 A1 | 6/1992 | |

(Continued)

OTHER PUBLICATIONS

English language abstract of DE 3232537 A1 dated Mar. 1, 1984.

*Primary Examiner* — Michael Logie

(57) ABSTRACT

In various embodiments, an emitter for the irradiation of surfaces is provided. The emitter may include: an emitter vessel and an emitter base connected thereto, wherein the emitter base has at least one gas opening, which is designed for supplying a process gas into a spatial area adjacent to the emitter vessel.

9 Claims, 2 Drawing Sheets

B-B

(56) References Cited

U.S. PATENT DOCUMENTS

| | | |
|---|---|---|
| 2005/0236997 A1* | 10/2005 | Danner et al. ............... 313/634 |
| 2005/0263719 A1* | 12/2005 | Ohdaira et al. ........... 250/492.1 |
| 2008/0061669 A1* | 3/2008 | Lomaev et al. ............... 313/113 |
| 2008/0265775 A1 | 10/2008 | Schiene et al. |
| 2009/0039757 A1* | 2/2009 | Ohshima et al. .............. 313/484 |
| 2010/0253207 A1* | 10/2010 | Joulaud et al. ................ 313/484 |

FOREIGN PATENT DOCUMENTS

| | | |
|---|---|---|
| EP | 0607960 A1 | 7/1994 |
| EP | 1601003 A2 | 11/2005 |
| EP | 1232518 B1 | 11/2006 |
| EP | 1506567 B1 | 7/2007 |
| EP | 1873810 A1 | 1/2008 |

* cited by examiner

A-A

RADIATING ELEMENT FOR IRRADIATING SURFACES, HAVING A SOCKET

RELATED APPLICATIONS

The present application is a national stage entry according to 35 U.S.C. §371 of PCT application No.: PCT/EP2011/068766 filed on Oct. 26, 2011, which claims priority from German application No.: 10 2010 043 215.6 filed on Nov. 2, 2010.

TECHNICAL FIELD

Various embodiments are based on an emitter having a base for the irradiation of surfaces with electromagnetic radiation. Furthermore, various embodiments relate to an emitter which emits short-wave ultraviolet (UV) radiation, e.g. below 200 nm. Such emitters can be used, inter alia, for sterilizing surfaces, for example flat films and the interior of bottles, canisters or other hollow containers.

BACKGROUND

It may be advantageous in the UV irradiation of surfaces, in particular sterilization, if flushing of the spatial area between the emitter and the surface using a flushing gas is performed at least during the irradiation, possibly also prior to and/or after said irradiation. This is intended to remove gases absorbing UV radiation between the surface to be irradiated and the UV emitter at least during the irradiation. A suitable flushing gas is in particular nitrogen or noble gases. A defined atmosphere between the emitter and the surface and consequently the use of a suitable process gas can be advantageous even in other irradiation processes. The term process gas is used in the text which follows as a generic term for one or more suitable gases for flushing or for other processes prior to, during and/or after the irradiation.

For the irradiation of easily accessible surfaces, for example flat films, the flushing gas has until now been supplied around the emitter or from the side by means of a separate device. Disadvantages here are the additional complexity involved in terms of apparatus and the necessary adaptation of the flushing arrangement and the emitter with respect to one another. In addition, these systems can generally not be used within cavities with narrow access openings such as canisters or bottles for reasons of space.

Document EP 1 506 567 B1 discloses a UV emitter on the basis of a single-sided dielectric barrier discharge. For this purpose, the discharge vessel 2 is filled with xenon. During the gas discharge, which is preferably operated by means of a pulsed operating method described in U.S. Pat. No. 5,604,410, so-called excimers are formed. Excimers are excited molecules, for example Xe2*, which emit electromagnetic radiation on reversal to the generally unbounded basic state. In the case of Xe2*, the maximum of the molecular band radiation is approximately 172 nm. In order to produce the dielectric barrier discharge, a first filament-like electrode 23 is arranged coaxially within the tubular discharge vessel 2. Six strip-shaped outer electrodes 8a-8f are arranged in parallel with one another and spaced apart from one another on the outer side of the discharge vessel 2.

Document EP 0 607 960 A1 discloses a tubular UV emitter on the basis of a two-sided dielectric barrier discharge. The emitter vessel is in the form of a coaxial double tube arrangement, in which an inner tube and an outer tube are connected to one another in gas-tight fashion at both end sides. The discharge space surrounded by the discharge vessel extends between the inner tube and the outer tube in this arrangement.

Document EP 1 232 518 B1 discloses a flat discharge lamp on the basis of a two-sided dielectric barrier discharge. The dielectric barrier discharge is produced between a bottom plate and a cover plate, wherein the surrounding sealing frame and funnel-shaped supporting elements are integrated in the cover plate. The electrodes are fitted as two mutually meshing comb-like line structures on the outer side of the bottom plate.

SUMMARY

Various embodiments provide an emitter which enables irradiation of surfaces under a defined atmosphere.

Various embodiments provide an emitter for the irradiation of surfaces, having an emitter vessel and an emitter base connected thereto, wherein the emitter base has at least one gas opening, which is designed for supplying a process gas into a spatial area adjacent to the emitter vessel.

Particularly advantageous configurations are given in the dependent claims.

In addition, protection is sought for the use of the emitter according to the invention for sterilizing flat or curved surfaces.

The basic concept of the invention consists in implementing the gas flushing with a process gas, for example an inert gas such as nitrogen or a noble gas, not with the aid of a separate device, but in developing an emitter in a suitable manner such that a process/flushing gas can emerge from the emitter and thus be supplied to the spatial area between the emitter and the surface to be irradiated. This reduces not only the complexity in terms of apparatus, but also the amount of time required, in particular during the irradiation of the inner faces of hollow bodies, where until now a gas exchange has generally been required prior to the irradiation. In addition, the space requirement for the device is reduced.

For this purpose, the emitter according to the invention is designed in such a way that the process gas flows out of the emitter base itself and in this way can be supplied to the adjacent spatial area of the surface to be irradiated. For this purpose, the emitter base has at least one gas opening, out of which the process gas can flow. Preferably, the at least one gas opening in the emitter base is arranged or aligned in such a way that the gas flow can flow in the direction of the emitter vessel or into the spatial area adjacent thereto.

In addition, provision can be made for the process gas to also flow through the emitter vessel and therefore likewise be supplied to the spatial area between the emitter and the surface to be irradiated. In this case, the process gas does not of course pass through the discharge space itself, in which a gas discharge produces the radiation during operation. Instead, the discharge space is also in this case hermetically sealed off by the discharge vessel. That is to say that the process gas flows possibly through one or more tunnel-like through-openings in the discharge vessel. As a result, the process gas can flow through the tunnel-like through-openings without influencing the gas discharge produced within the hermetically sealed discharge vessel. In this case, provision can also be made for a switchover to be possible, at least temporarily, from gas supply to gas discharge.

In addition, one or more gas openings or tunnel-like through-openings can also generally be provided for the gas discharge. This is advantageous in particular for the sterilization of hollow containers such as bottles or canisters with narrow container openings, where little space remains for the process gas to flow away, under certain circumstances. In one development of the emitter according to the invention, a seal is additionally provided between the emitter and the container opening in order to prevent the ingress of ambient air into the container. Here, the process gas flows away exclusively via the gas opening(s) or through-opening(s) provided for this purpose in the emitter.

For the irradiation of hollow containers such as bottles or canisters with narrow container openings, the emitter and in particular the emitter vessel is elongate in order to be able to be introduced via the sometimes narrow opening in the container.

An emitter with an emitter vessel which includes an inner tube and an outer tube which are connected to one another in gas-tight fashion in the manner of a coaxial double tube arrangement is particularly suitable for this purpose. Since in this arrangement, the discharge space surrounded by the discharge vessel extends between the inner and the outer tube, the interior of the inner tube can additionally be used as tunnel-like through-opening for the flow of process gas. For this purpose, the process gas is supplied at one end of the inner tube and emerges again at the other end of said inner tube. As a result, the process gas also emerges on the end side of the emitter vessel and therefore in the direct vicinity of the radiation or the surface to be irradiated. Alternatively, the inner tube can also be provided for discharging the process gas. This has the advantage that the base does not additionally need to be designed for the discharge of the process gas, i.e. via one or more additional gas discharge openings in the base designed for this purpose.

For the supply with process gas, the emitter is preferably provided with a connection, to which a gas line can be connected. Alternatively, the emitter can also be connected directly to a gas line.

As well as being suitable for the irradiation of hollow containers, the elongate emitter is generally also suitable for irradiating extended, for example planar faces, for example foil webs. For the latter case, however, an alternative embodiment is also particularly suitable, wherein the emitter and in particular the emitter vessel have a flat shape. In other words, this alternative is based on a so-called flat lamp, which has been modified possibly for the desired radiation, in particular UV radiation for the sterilization. In this embodiment too, the emitter base, which is frame-shaped for example in this case, has at least one gas opening, out of which the gas flow can emerge. Additionally, the flat emitter vessel itself can also be provided with tunnel-like through-openings for the process gas. For further details, reference is made to the exemplary embodiments shown in the figures.

In general, the emitter vessel consists at least sectionally of a material which is transparent to the radiation, in the case of UV radiation preferably quartz glass.

For the generation of UV radiation, the emitter is preferably designed for a dielectric barrier discharge in the interior of the emitter vessel. For further details in this regard, reference is made to the documents EP 1 506 567 B1, U.S. Pat. No. 5,604,410 and EP 1 232 518 B1 mentioned at the outset.

BRIEF DESCRIPTION OF THE DRAWINGS

The invention will be explained in more detail below with reference to exemplary embodiments. In the figures:

FIG. 2b shows an illustration of a longitudinal partial section through the emitter shown in FIG. 2a.

DETAILED DESCRIPTION

The following detailed description refers to the accompanying drawings that show, by way of illustration, specific details and embodiments in which the invention may be practiced.

Figure 1A:
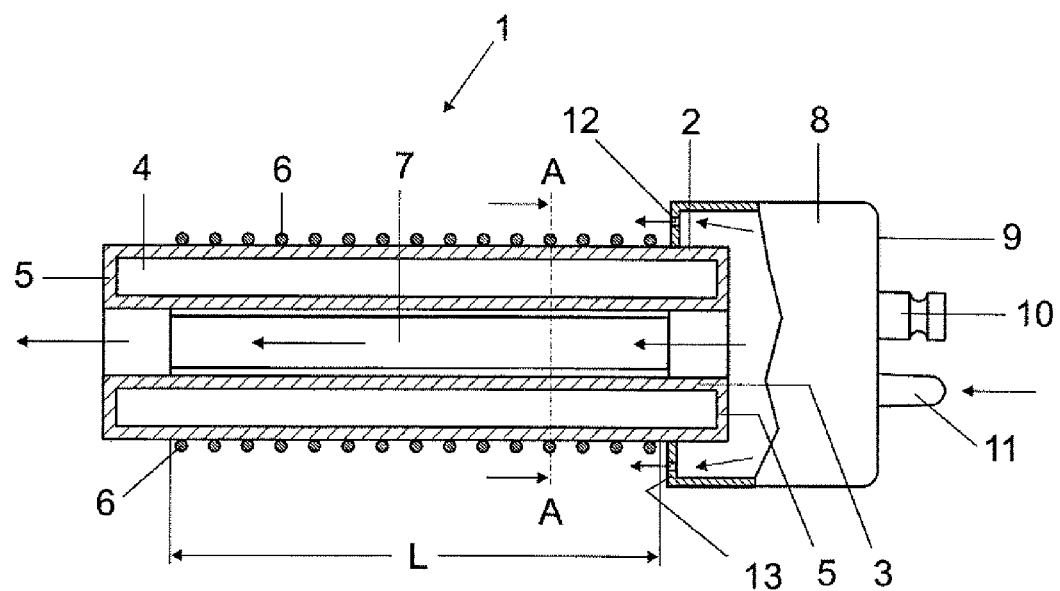
FIG. 1a shows an illustration of a longitudinal partial section through a tubular emitter according to the invention.
Figure 1B:
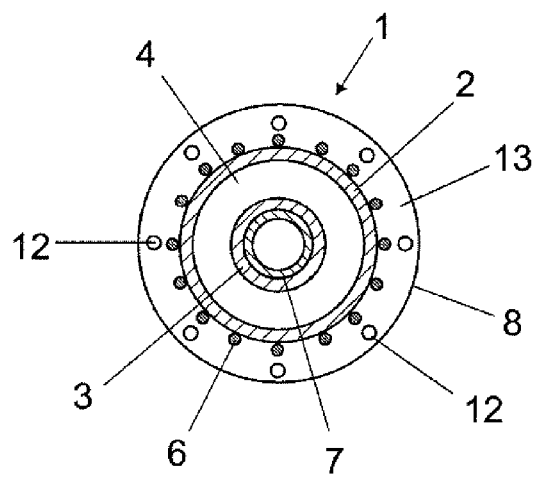
FIG. 1b shows a cross-sectional illustration of the emitter shown in FIG. 1a, FIG. 2a shows a plan view of a flat emitter according to the invention.

FIGS. 1a and 1b show, in very schematized illustrations, a partially sectioned longitudinal view or a cross-sectional view of a first exemplary embodiment of the emitter 1 according to the invention on the basis of a dielectric barrier discharge. The elongate discharge vessel of the emitter 1 includes an outer tube 2 and an inner tube 3 with a coaxial double tube arrangement, which outer and inner tubes thus define the longitudinal axis of the discharge vessel. The length of the tubes varies depending on the application. For the sterilization of bottles, for example, the length is preferably dimensioned such that the bottle inner face is completely irradiated when the emitter is dipped in. The diameters of the tubes are likewise preferably matched to the application. In particular, the largest outer diameter of the discharge vessel is dimensioned such that the emitter 1 can be introduced into the container intended for the irradiation, for example through the bottle neck into a bottle. Both tubes 2, 3 consist of quartz glass which is permeable to UV radiation. In addition, the discharge vessel is sealed at both of its end sides in such a way that an elongate discharge space 4 in the form of an annular gap is formed. For this purpose, the discharge vessel has ring-like vessel sections 5 each with a suitable formation at both ends of said discharge vessel. In addition, an exhaust tube (not illustrated) is attached to one of the vessel sections 5 and is used firstly to evacuate the discharge space 4 and then to fill the discharge space with 15 kPa of xenon. A wire mesh 6 is drawn over the outer side of the wall of the outer tube 2 and forms the outer electrode of the lamp 1. Alternatively, a narrow helical metal web can also be applied for this purpose, for example. A metal tube 7, which forms the inner electrode of the lamp, is arranged in the interior of the inner tube 3, i.e. likewise outside the discharge space 4 surrounded by the discharge vessel. Alternatively, a conductive layer, for example consisting of carbon, can also be applied for this purpose, for example. A pot-shaped base 8 is arranged at one end of the discharge vessel. The end side 9 remote from the discharge vessel has an electrical jack 10 for connecting the supply voltage for the emitter 1. In addition, a gas connecting pipe 11 is fitted on the end side 9, and a process gas flexible hose can be plugged onto said gas connecting pipe. The process gas flowing in via the gas connecting pipe 11 passes in the interior of the base 8 to in total eight holes 12, which are arranged distributed uniformly over the circumference in the ring-shaped base projection 13, out of which the discharge vessel protrudes. As a result, the process gas can emerge from these holes 12 and flow along the outer tube 2 to the adjacent spatial area thereof. In addition, the base 8 is formed in the interior in such a way that the process gas can flow in at the base-side end of the inner tube 3 and flow out at the other end of said inner tube. The inner tube therefore acts additionally as tunnel-like through-opening through the discharge vessel for the process gas. Alternatively, the inner tube can also be provided for the discharge of the process gas and/or some of the gas openings in the base.

Figure 2A:
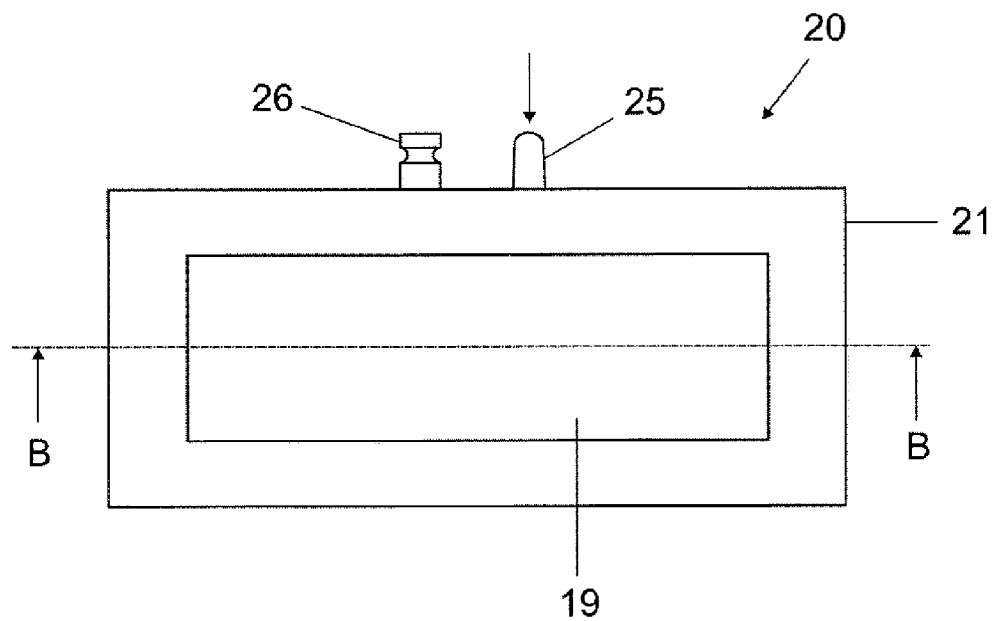
Figure 2B:
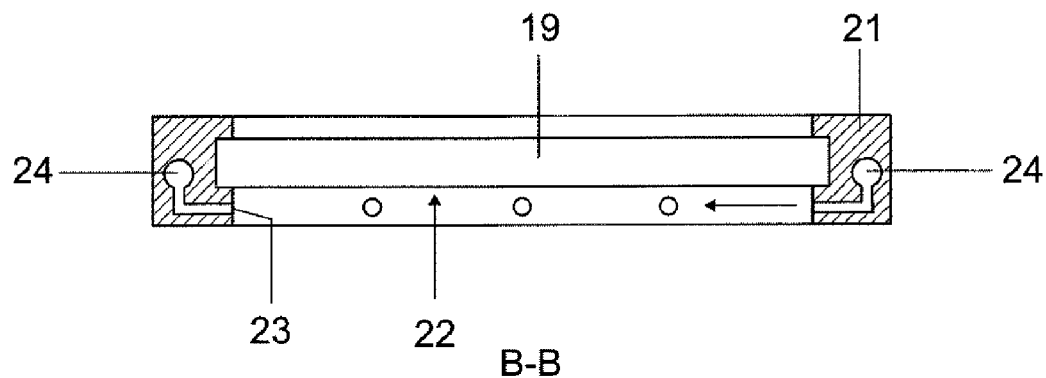

FIGS. 2a and 2b show, in very schematized illustration, a plan view of and a partial longitudinal section through a flat emitter 20 according to the invention. This emitter has a flat emitter vessel 19 and an emitter base 21, which encloses the flat emitter vessel 19 in the form of a frame. The emitter vessel 19 is a modified flat lamp (not shown in section) on the basis of a dielectric barrier discharge as is known, for example, from EP 1 232 518 B1 mentioned at the outset. For the sterilization by means of UV radiation, the otherwise convention phosphor is dispensed with. In addition, the flat discharge vessel consists of quartz glass owing to the required transparency for UV radiation. The discharge vessel itself has a rectangular basic shape. The electrodes of the emitter vessel are designed as is known for these lamp types and are not illustrated here for reasons of clarity. The emitter base 21 protrudes in particular beyond the front side 22 of the emitter vessel which emits the radiation. There, a plurality of gas openings 23 are arranged on the protruding inner sides of the frame-shaped emitter base 21 in such a way that the process gas can flow from the side over the front side 22 of the flat emitter and consequently also via the surface to be irradiated which is directly adjacent during the irradiation. The in particular eight gas openings 23 (2 times 1 for both narrow sides plus 2 times 3 for the two long sides) are fed via a ring gas line 24, which is in turn connected to a gas connection connecting pipe 25 arranged on the emitter base 21. In addition, the emitter base 21 has an electrical jack 26 for connection of the supply voltage for the operation of the flat emitter. In one variant which is not illustrated, the flat emitter vessel is provided with tunnel-like through-openings, which enable an additional gas flow through the flat emitter vessel, i.e. substantially perpendicular to the surface to be irradiated. The tunnel-like through-openings can be provided, for example, in the case of a flat lamp of the type disclosed in EP 1 232 518 B1 mentioned at the outset by breaking through in gas-tight fashion one or more of the funnel-like supporting points formed from the flat vessel parts. The tunnel-like through-openings in the flat emitter vessel can alternatively also be provided for the discharge of the process gas.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An emitter for the irradiation of surfaces, the emitter comprising:
an emitter vessel and an emitter base connected thereto,
wherein the emitter base has a plurality of gas openings, which are designed for supplying a process gas into a spatial area adjacent to the emitter vessel;
wherein the emitter vessel is flat;
wherein the emitter base is in the form of a frame;
wherein the emitter base protrudes beyond a radiation emitting front surface area of the emitter vessel, the protrusion comprising an inner side located adjacent to the radiation emitting front surface area;
and wherein a plurality of gas openings are arranged on the inner side.

2. The emitter as claimed in claim 1,
wherein the at least one gas opening is arranged and oriented in such a way that the process gas can flow into a spatial area adjacent to the emitter vessel.

3. The emitter as claimed in claim 1,
wherein the emitter vessel is provided with at least one tunnel-like through-opening, which is provided for supplying or discharging the process gas.

4. The emitter as claimed in claim 1, further comprising:
a gas connection for the supply of process gas.

5. The emitter as claimed in claim 1,
wherein the emitter base has at least one gas opening, which is designed for the discharge of a process gas.

6. The emitter as claimed in claim 1,
wherein the emitter vessel consists at least sectionally of a material which is transparent to the radiation.

7. The emitter as claimed in claim 1,
which is designed for the emission of UV radiation.

8. The emitter as claimed in claim 1,
which is designed for a dielectric barrier discharge in the interior of the emitter vessel.

9. A use of an emitter for sterilizing flat surfaces, the emitter comprising:
an emitter vessel and an emitter base connected thereto,
wherein a process gas is supplied into a spatial area adjacent to the emitter vessel through a plurality of gas openings of the emitter base;
wherein the emitter vessel is flat;
wherein the emitter base is in the form of a frame;
wherein the emitter base protrudes beyond a radiation emitting front surface area of the emitter vessel, the protrusion comprising an inner side located adjacent to the radiation emitting front surface area;
and wherein a plurality of gas openings are arranged on the inner side.

* * * * *